United States Patent
Qiu

(10) Patent No.: US 9,073,989 B2
(45) Date of Patent: Jul. 7, 2015

(54) ANTIBIOTIC COMPRISING AN ANTIBODY MIMETIC, ITS PREPARATION METHODS AND USES THEREOF

(75) Inventor: Xiaoqing Qiu, Beijing (CN)

(73) Assignee: PROTEIN DESIGN LAB, LTD, Beijing (CN)

( * ) Notice: Subject to any disclaimer, the term of this patent is extended or adjusted under 35 U.S.C. 154(b) by 876 days.

(21) Appl. No.: 13/013,693

(22) Filed: Jan. 25, 2011

(65) Prior Publication Data

US 2012/0190826 A1  Jul. 26, 2012

(51) Int. Cl.
| | |
|---|---|
| *C07K 14/24* | (2006.01) |
| *C07K 14/245* | (2006.01) |
| *C07K 16/12* | (2006.01) |
| *A61K 47/48* | (2006.01) |
| *A61K 39/00* | (2006.01) |
| *A61K 38/00* | (2006.01) |

(52) U.S. Cl.
CPC ......... *C07K 14/245* (2013.01); *A61K 2039/505* (2013.01); *C07K 16/1217* (2013.01); *C07K 2317/567* (2013.01); *C07K 2317/569* (2013.01); *C07K 2317/60* (2013.01); *C07K 2319/01* (2013.01); *C07K 2319/30* (2013.01); *A61K 38/00* (2013.01); *A61K 47/48484* (2013.01); *A61K 47/48507* (2013.01); *C07K 2317/565* (2013.01)

(58) Field of Classification Search
None
See application file for complete search history.

(56) References Cited

PUBLICATIONS

Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
[Fundamental Immunology p. 242 (William E. Paul, M.D. ed., 3d ed; 1993)].*
Qiu et al, Major transmembrane movement associated with Colicin la channel gating. J. Gen. Physiology, 107: 313-328 (1996).

* cited by examiner

*Primary Examiner* — Brad Duffy
(74) *Attorney, Agent, or Firm* — Maschoff Brennan

(57) ABSTRACT

The present invention belongs to field of biology and medicine, and especially relates to a novel antibiotic comprising an antibody mimetic antibody, its preparation methods and uses thereof. A novel antibiotic comprising a antibody mimetic covalently bonded to the carboxyl end of a colicin polypeptide or a channel-forming domain polypeptide of a colicin, wherein said colicin is selected from the group consisting of Colicin E1, Ia, Ib, A, B, N; wherein said antibody mimetic being yielded by fusing two complementarity determining regions (CDRs), $V_H CDR_1$ and $V_L CDR3$ through a cognate framework region ($V_H FR_2$) of an immunoglobulin; wherein said immunoglobulin specifically recognizes the bacterial porins. Its antibacterial ability is a thousandfold powerful than normal antibiotics. Due to its unique action mechanism, drug resistance resulted in mutation can hardly be acquired by pathogenic bacteria. And the antibiotic will not hurt normal human cells when it kills pathogenic bacteria. Therefore, it can be used for manufacturing antibacterial medicament of killing *Neisseria meningitidis*, vancomycin-resistant *Enterococcus faecalis*, methicillin-resistant *Staphylococcus aureus*, multidrug-resistance *Pseudomonas aeruginosa* or *Mycobacterium tuberculosis*.

11 Claims, 6 Drawing Sheets

Fig.1

Inserted gene encoding peptide:
SYWLHWIKQRPGQGLWIGSQST
HVPRT

Fig.2

Inserted gene encoding peptide:
SYWLHWIKQRPGQGLWIGTRPV
HTSQS

Fig.3

H₂N — [ T ] — [ R ] — [ Channel-forming ] — [ antibody mimetic ] — COOH

ANTIBIOTIC COMPRISING AN ANTIBODY MIMETIC, ITS PREPARATION METHODS AND USES THEREOF

FIELD OF THE INVENTION

The present invention belongs to the domain of biology and medicine, and especially relates to a novel antibiotic comprising an antibody mimetic, its preparation methods and uses thereof.

RELATED ART

Since Penicillin and other antibiotics were brought into use in 1944, *Diplococcus meningitides*, and other life-threatening pathogenic bacteria such as *Staphylococcus aureus, Streptococcus pneumoniae, Pseudomonas aeruginosa*, and *Neisseria meningitidis* have acquired drug resistance. According to relative reports published by United States Disease Control Center (CDC) in recent years, these antibiotics would be likely to lose effectiveness completely in 10 or 20 years.

The present antibiotics kill pathogenic bacteria by restraining synthesis of cell wall, restraining or interfering the pathway of bacterial nucleic acid and protein metabolism and synthesis. However, these antibiosis methods are more likely to lead to drug resistance resulted by bacteria mutation. Therefore scientists are dedicated to develop novel antibiotics. One of the comparatively promising directions is to imitate the inter-killing mechanism among homogeneous heterologous strains so as to develop novel antibiotics. In Nature, a number of bacterial toxins can directly form ion channels on bacteria cytomembrane to kill bacteria. The typical specimen is a kind of bacterial toxin secreted by *E.col*, colicin. One of which is Colicin Ia, found in 1952 by Jacob. After efforts of generations, the transmembrane spatial structure of Colicin Ia when ion channels open as well as shut on the artificial lipide bimolecular film (Qiu et al, Major transmembrane movement associated with Colicin Ia channel gating. J. Gen. Physiology, 107: 313-328 (1996)) was disclosed in 1996. This established theoretical laid the basis for designing and preparing novel antibiotics on molecular level.

As mentioned above, colicin is a kind of ideal ion channel antibiotic model, but wild-type colicin can only act on homogeneous heterologous strains. We must change the targeting of the colicin so that they are capable of acting on other pathogenic bacteria. Porin, a kind of pore protein existing on the outer membrane of bacteria, mitochondria or chloroplast, allows bigger molecules to pass through. Porin also has a higher immunogenicity, and can induce high level expression of monoclonal antibody in host cells. It should be an ideal development direction for antibody research, if we can design an antibody mimetic with better recognizing ability to change the targeting of the colicin, by using the antibody specific for porins on outer membran of bacteria as the antetype of the antibody mimetic.

SUMMARY OF THE INVENTION

To overcome the above technical defects and make up a deficiency in the art, the present invention provides a novel antibiotic. Its antibacterial ability is a thousand-fold more powerful than regular antibiotics. Due to its unique action mechanism, drug resistance resulted in mutation can hardly be acquired by pathogenic bacteria. And the antibiotic will not hurt normal human cells when it kills pathogenic bacteria.

A novel antibiotic comprising an antibody mimetic covalently bonded to the carboxyl end of a colicin polypeptide or a channel-forming domain polypeptide of a colicin, wherein said colicin is selected from the group consisting of colicin E1, Ia, Ib, A, B, N; wherein said antibody mimetic being yielded by fusing two complementarity determining regions (CDRs), $V_H CDR_1$ and $V_L CDR3$ through a cognate framework region ($V_H FR_2$) of an immunoglobulin; wherein said the immunoglobulin specifically recognizes the bacterial porins.

Wherein said bacterial porins are PorA in the outer membrane of *Neisseria meningitidis* cells.

Wherein said immunoglobulin has a Fab consisting of a heavy chain (2MPA H) and a light chain (2MPA L).

Wherein said the colicin is Ia.

The fusion peptide molecules of any of the novel antibiotics.

One of the foresaid fusion peptide molecules with the amino acid sequence set forth in SEQ ID NO.6.

The nucleic acid molecules encoding any of the fusion peptide molecules.

Wherein said nucleic acid molecule with nucleotide sequence set forth in SEQ ID NO.5.

The recombinant plasmids comprising any of foresaid nucleic acid molecules.

The preparation methods of the foresaid novel antibiotics, any of foresaid recombinant plasmids is transfected into an expression system, and the polypeptide is separated and purified to obtain the novel antibiotic.

The use of any of foresaid novel antibiotics for preparing antibacterial medicament.

Wherein said antibacterial medicament is used for killing *Neisseria meningitidis*, vancomycin-resistant *Enterococcus faecalis*, methicillin-resistant *Staphylococcus aureus*, multi-drug-resistance *Pseudomonas aeruginosa* or *Mycobacterium tuberculosis*.

The novel antibiotics of this invention are based on the foundation of colicin's characteristic of forming ion channels on the target pathogen membrane, which causes the pathogen to leak out its content and die. The targeting structure is an antibody mimetic with some domains of an immunoglobulin specifically recognizing porin protein on target pathogen. The antibody mimetic being yielded by fusion of two complementarity determining regions (CDRs), $V_H CDR_1$ and $V_L CDR3$, through a cognate framework region ($V_H FR_2$) of an immunoglobulin The three domains covalently form a linear peptide molecule as $V_H CDR1$-$V_H FR2$-$V_L CDR3$ from amino end to carboxyl end. It is well known that the active regions of an immunoglobulin for recognition reaction are called complementary determining region which has only about several to a dozen of amino acid, and have smaller molecular weight, nicer tissue penetration and simpler structure without most parts of frame structure and Fc fragment of a nature antibody than nature antibody molecule or present artificial reconstructed antibody such as seFv and Fab, so it will reduce immune response level in patients and easily guide the colicin of the novel antibiotic to reach infected tissues and identify the pathogenic bacteria. In clinical application, the novel antibiotic is directed to membrane of the target pathogenic bacteria, and the colicin contained forms ion channels on bacteria cytomembrane of the target bacteria and kills the target bacteria because of the leak-out of its cytoplasm. The antibacterial ability of the novel antibiotic also applies to bacterial strains with drug resistance. As the recognition sites are unique antigenic properties on bacterial surface, there are no such recognition sites on human cytomembrane, and the novel antibiotic is safe for human. Compared to other antibiotics easily to cause drug resistance, the antibiotic in this invention kills the pathogenic bacteria not by the porin but by the colicin acting on biomembrane of the pathogenic bacteria and forming ion channels to make the cell leaking out the cytoplasm to die. The antibody mimetic for targeting just needs to guide the colicin to the pathogenic bacteria. Bacteria's drug resistance is normally acquired by changing porin's structure and creating barrier for antibiotic's entry. The antibiotic in this invention only requires porin's antibody recognition sites for purpose of killing the pathogenic bacteria. The novel antibiotics identify the sites of porin on the membrane of bacteria, but the colicin of the novel antibiotic binds on other sites and forms ion channels to make the bacteria to leak out to die. The action sites are not the porin. So the pathogenic bacteria is not likely to acquire drug resistance to the novel antibiotic by mutating, evolving, throwing away or changing the structure of porin which is necessary for survival. According to this inventive concept, the novel antibiotic has many variants due to the diversity of porin on bacterium surface and the diversity of the immunoglobulin recognizing the porins.

Since the meningitis caused by *Neisseria meningitidis* seriously threatens infants and children's health at home and abroad, the drug resistance of *Neisseria meningitidis* to common medicine is very serious, and the dosage is higher and higher in order to inhibit the bacteria efficiently, which seriously endangers the health of patients. Therefore, on the basis of foresaid inventive concept of this invention, the inventor reconstructed and obtained an antibody mimetic of the antibody which was specific for the porin A of *Neisseria meningitidis*. The heavy chain peptide of the antibody had an accession number: 2MPA_H at PubMed Home. The light chain peptide had an accession number: 2MPA_L at PubMed Home. The antibody mimetic, its amino acid sequence set forth in Seq ID No.2, was connected on the C-terminus of the Colicin Ia's peptide to constitute a novel antibiotic PMC-AM1 with amino acid sequence set forth in Seq ID No.6. As survival curve of mice shown in FIG. 7, the survival rate of the mice injected with fatal dose of *Neisseria meningitides* in PMC-AM1 group was 90% in 8 days. It showed that the antibacterial activity and protective effect in vivo of the novel antibiotics are superior to current normal antibiotics such as penicillin and gentamicin. Meanwhile a comparative test on bactericidal effect was set to compare the minimum inhibitory concentration (MIC value) of PMC-AM1, ceftazidime and ampicillin for *Neisseria meningitidis*. As shown in FIG. 6A, the MIC value of PMC-AM1 was 0.11 nMol, ceftazidime was 3.02 nMol and ampicillin was 1.35 nMol. This result indicated that the bactericidal ability of PMC-AM1 is significantly more powerful than antibiotics currently used for inhibiting *Neisseria meningitidis*.

After that, experiments were set to test the bactericidal effect of the novel antibiotic PMC-AM1 on other pathogens with serious drug-resistance. The result showed that the PMC-AM1 had extremely stronger antibacterial ability on multi-drug resistant *Pseudomonas aeruginosa,* vancomycin-resistant *Enterococcus faecalis*, methicillin-resistant *Staphylococcus aureus*. As shown in FIG. 5, its antibacterial ability was 127 to 3800 times stronger than that of ceftazidime, levofloxacin, gentamicin etc. And as shown in FIG. 6B and FIG. 6C, PMC-AM1 has obvious antibiosis effect on multidrugresistant *Pseudomonas aeruginosa*, vancomycin-resistant *Enterococcus faecalis*, methicillin-resistant *Staphylococcus aureus*.

In another embodiment, we found that the PMC-AM1 had extremely stronger antibacterial ability on rifampin-resistant *Mycobacterium tuberculosisas*, as shown in FIG. 9~FIG. 11.

The novel antibiotic of this invention can be used to prepare antibacterial drugs, especially for *Neisseria meningitidis,* *Pseudomonas aeruginosa*, vancomycin-resistant *Enterococcus faecalis,* methicillin-resistant *Staphylococcus aureus* or *Mycobacterium tuberculosis*.

The nucleotide sequences encoding the peptides of the novel antibiotics can be cloned into the expression vector to construct recombinant plasmids which express fusion protein in host cell. The isolated fusion protein is the novel antibiotic protein of this invention.

According to degeneracy of nucleotide codons, the nucleotide sequence encoding antibiotic of the invention is adjustable. One of skill in the art would be able to adjust the nucleotide sequence according to the host cells' preference to the nucleotide codon. As long as the encoded polypeptide has no change, the nucleotide sequences are still in the scope of inventive concept of this invention.

BRIEF DESCRIPTION OF THE DRAWINGS

FIG. 1 shows the structure of recombinant plasmid comprising the gene of antibody mimetic and gene of Colicin Ia, referred to herein as pBHC-PorA1. In the fusion peptide expressed by the recombinant plasmid, the peptide of the antibody mimetic bonded to the C-terminus of Colicin Ia, and the amino acid sequence of the antibody mimetic is set forth in Seq ID No.2.

FIG. 2 shows the structure of the recombinant plasmid comprising the gene of antibody mimetic and gene of Colicin Ia, referred to herein as pBHC-PorA2, In the fusion peptide expressed by the recombinant plasmid, the peptide of antibody mimetic is linked to the C-terminus of Ia's peptide, and the amino acid sequence of the antibody mimetic set forth in Seq ID No.4. In the antibody mimetic, a $V_H$CDR1 and a reversed $V_L$CDR3 are connected through a cognate framework region ($V_H FR_2$).

FIG. 3 illustrates the construction of the novel antibiotic. In which, T and R are signal recognition domains on the N-terminus of Colicin Ia. The channel-forming, a structure field capable of forming Ion channels, is situated at C-terminus of Colicin Ia. The AM is an antibody mimetic.

In which, the longitudinal ordinate shows minimum inhibitory concentration (nMol); A shows the result of *Nesseria meningitidi*: (1) PMC-AM1, MIC=0.11 nMol, (2) ceftazidime, MIC=3.02 nMol, (3) ampicillin, MIC=1.35 nMol; B shows the result of vancomycin-resistant *Enterococcus faecalis* (1) PMC-AM1, MIC=0.23 nMol, (2) vancomycin, MIC=21.54 nMol, (3) ampicillin, MIC=10.78 nMol; C shows the result for methicillin-resistant *Staphylococcus aureus:* (1) PMC-AM1, MIC=0.06 nMol, (2) ampicillin, MIC=21.55 nMol, (3) oxacillin, MIC=14.1 nMol; D shows the result for multi-drug resistant *Pseudomonas aeruginosa:* (1) PMC-AM1, MIC=0.91 nMol, (2) levofloxacin, MIC=43.2 nMol, (3) ceftazidime, MIC=29.3 nMol, (4) gentamicin, MIC>889.4 nMol.

Figure 7:
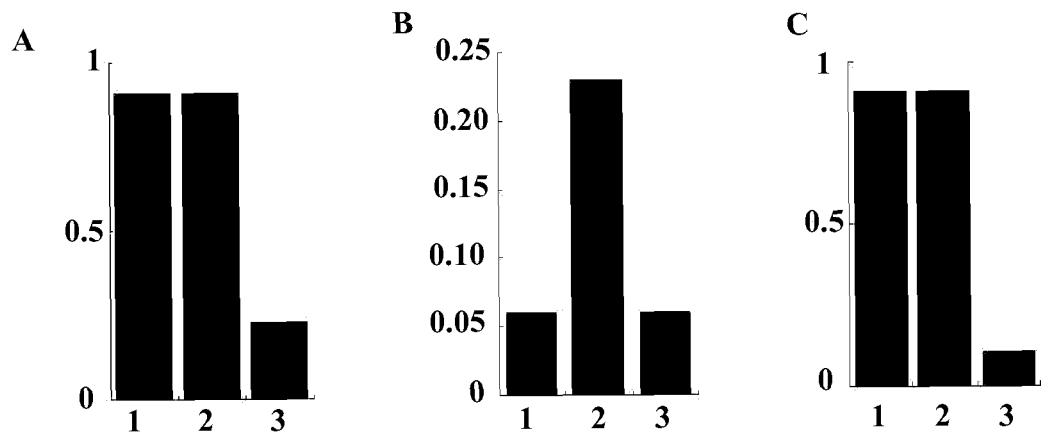

FIG. 7 shows survival curve of comparison of inhibition effective of the novel antibiotic, the wild-type colicin and the polypeptide anti-*Staphylococcal aureus* disclosed in China patent ZL 01128836.1 on methicillin-resistant *Staphylococcus aureus* (ATCC BAA-42), vancomycin-resistant *Enterococcus faecalis* (ATCC 700802), and multi-drug resistant *Pseudomonas aeruginosa* (isolated by West China Hospital, No. 13578). In which, longitudinal ordinate shows minimum inhibitory concentration(nMol); A shows the result for vancomycin-resistant *Enterococcus faecalis:* (1) the polypeptide anti-*Staphylococcus aureus*, MIC=0.91 nMol, (2) the wild-type Colicin Ia, MIC=0.91 nMol, (3) PMC-AM1, MIC=0.23 nMol; B shows the result for methicillin-resistant *Staphylococcus aureus:* (1) the polypeptide anti-*Staphylococcus aureus*, MIC=0.06 nMol, (2) the wild-type Colicin Ia, MIC=0.23 nMol, (3) PMC-AM1, MIC=0.06 nMol. C shows the result for multidrug resistance *Pseudomonas aeruginosa:* (1) the polypeptide anti-*Staphylococcus aureus,* MIC=0.91 nMol, (2) the wild-type Colicin Ia, MIC=0.91 nMol, (3) PMC-AM1,MIC=0.23 nMol.

Figure 8:
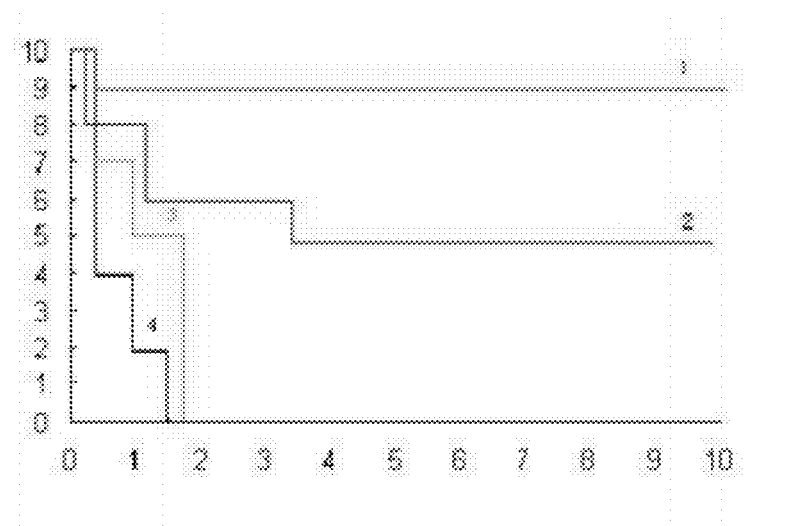

FIG. 8 shows survival curves which were the result of in vivo experiment of the novel antibiotics to protect animals infected by *Nesseria meningitidis*. In which, horizontal ordinate shows the survival time of mice, in days; Longitudinal ordinate shows the number of animal survival. 1) PMC-AM1; 2) Gen was gentamicin; 3) PEN was penicillin; 4) Con. was blank control. The injection concentration of all test drugs is by 1.5 mg/kg (drug's weight/mouse's weight).

Figure 9:
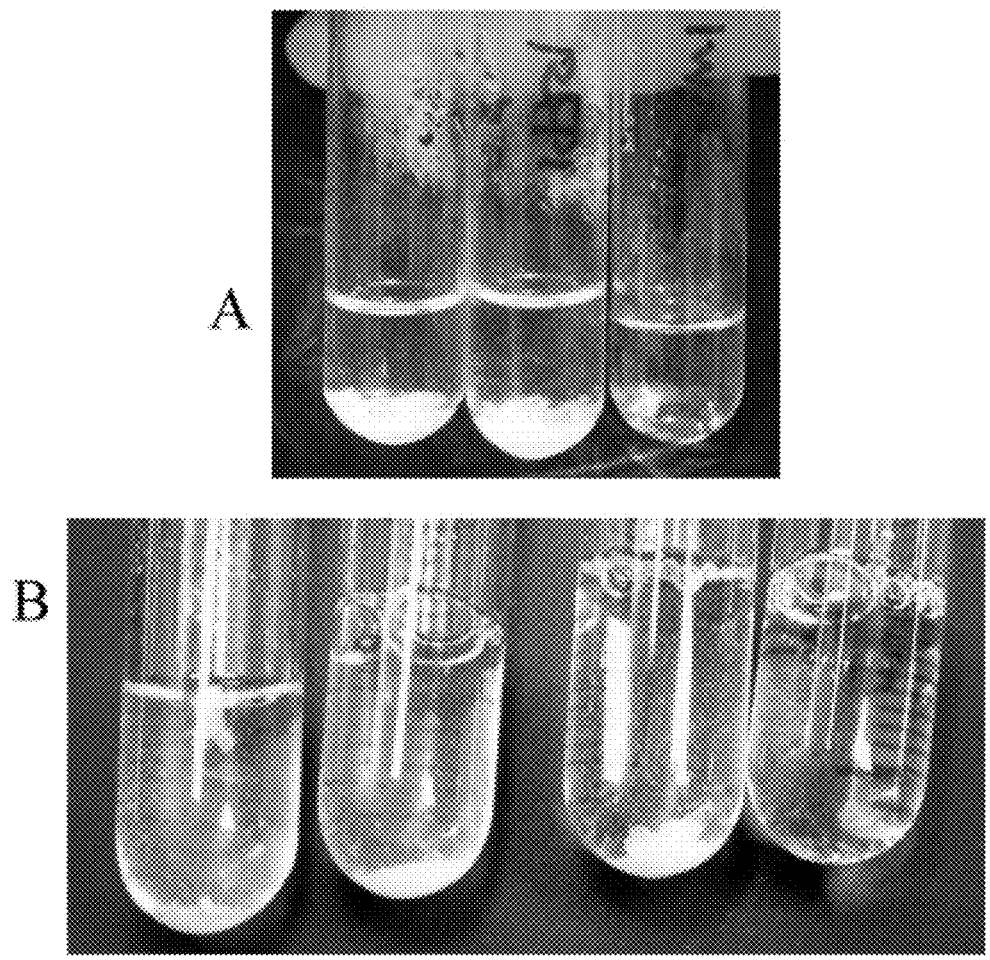

FIG. 9 shows the effect of the PMC-AM1 on the growth of *Mycobacterium tuberculosisas*.

In FIG. 9A, the left tube was the control added in 0.3 M NaCl+50 mM boric acid buffer; the middle tube was a treatment added rifampicin. The two treatments all showed a mass of cell growth on bottom of the tube. The right tube is a treatment added PMC-AM1, and there was no cell growth. In FIG. 9B, the first tube on left was blank control, the second tube on left was the control added 0.3 M NaCl+50 mM boric acid buffer, the third tube was a treatment added wild-type Colicin Ia; the three treatments all showed quantity of cells growth on bottom of the tubes. The right one was a treatment added bacteria culture solution of PMC-AM1 group which has no growth of bacteria lawn, and there was still no cell growth in this tube.

Figure 10:
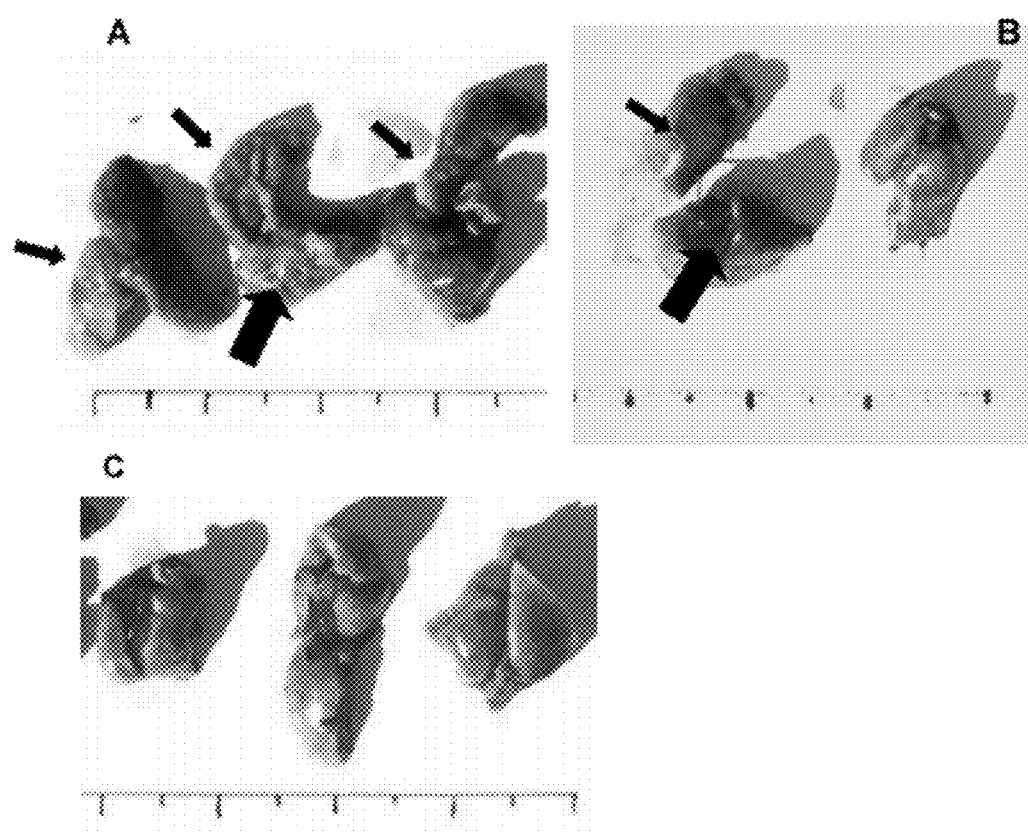

FIG. 10 shows survival curve of in vivo experiments of the novel antibiotics to protect animals infected by *Mycobacterium tuberculosis*.

In which, A shows the lungs of three control mice, arrows indicating TB nodules; B shows the lungs of mice treated by rifampicin, one of which can be seen tissue necrosis (as arrows indicate); C shows the lungs of three mice treated by PMC-AM1, which were intact, and had no nodules and necrosis of tuberculosis.

Figure 11:
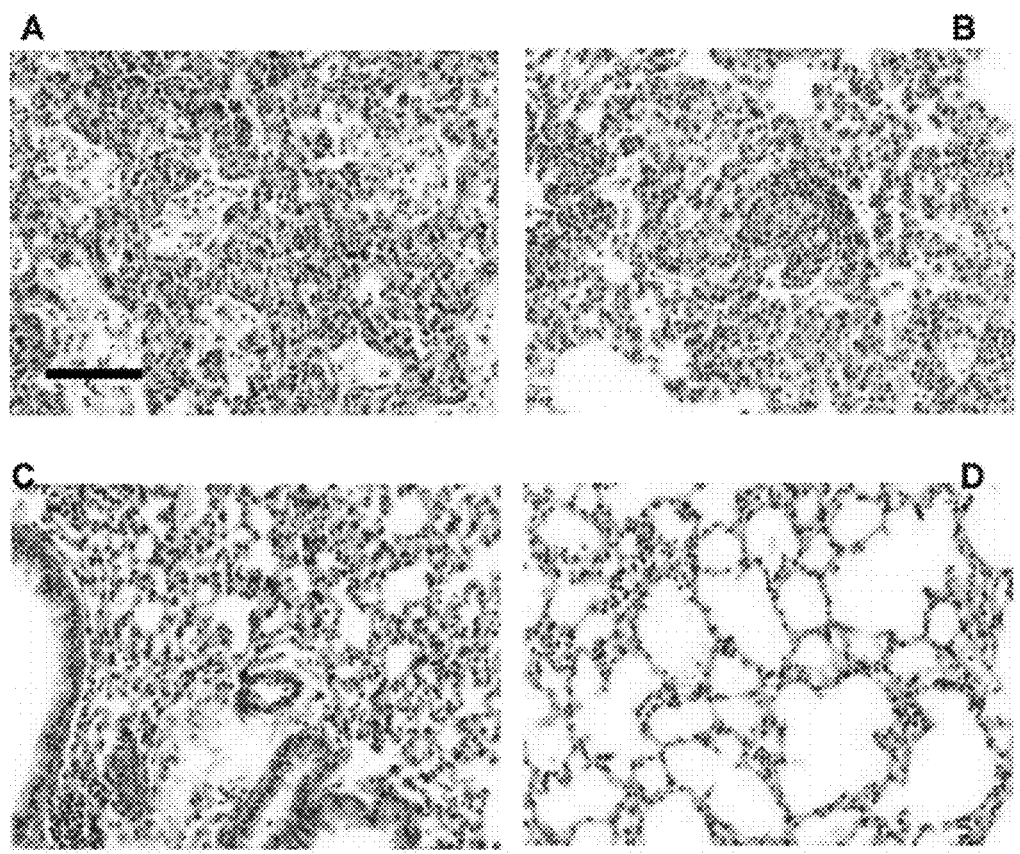

FIG. 11 shows survival curve of in vivo experiments of the novel antibiotics to protect animals infected by *Mycobacterium tuberculosis*.

A shows the lung of a control mouse; B shows the lung of a mouse treated by wild-type Colicin Ia; C shows the lung of a mouse treated by rifampicin; D shows the lung of a mouse treated by PMC-AM1.

Magnification was 200; scale in FIG. A was 100 μm.

Embodiments

The invention is further illustrated by the following embodiments as well as the drawings.

Embodiment 1: Construction of Plasmids Expressing the Novel Antibiotics and Preparation of the Novel Antibiotics The original plasmid was pSELECT™-1 plasmid (8.3 kb) (purchased from Promega corporation) with genes of Colicin Ia and immunity protein. By Double Strands Oligo nucleotide Point Mutation Technology (QuickChange™ Kit, Strategene corporation) the gene encoding the antibody mimetic set forth in SEQ ID NO. 1 or 3 were inserted to 626 amino acid position of Colicin Ia gene, and two recombinant plasmids, herein referred to as pBHC-PorA1 and pBHC-PorA2shown in FIG. 1 and FIG. 2, were constructed, which were used to prepare the novel antibiotics. The recombinant plasmids were transfected into *E.coli* BL-21 engineering bacterium to prepare the novel antibiotics.

The mutation procedure was proceeded according to the manual of Strategene Quick Change Site Directed Mutagenesis Kit (catalog #200518):

1. Point mutation reactant was prepared:
   5 μl 10× buffer
   2 μl (10 ng) original plasmid pSELECT™-1 with genes of Colicin Ia and immunity protein.
   1.25 μl (125 ng) artificial 5'-3' oligo nucleotide primer (refer to the primers Sequence ID No.9, 11, 13, 15, 17, 19)
   1.25 μl (125 ng) artificial 3'-5' oligo nucleotide primer (refer to the primers Sequence ID No.10, 12, 14, 16, 18, 20)
   1 μl dNTP
   50 μl de-ionized water
   1 μl Pfu
   (The above drugs were all reagents in the medical kit, except plasmid, primer and de-ionized water.)

2. PCR amplification was proceeded with the amplification conditions as follow: denaturalize at 95° C. for 35 seconds, anneal at 53° C. for 70 seconds, extend at 68° C. for 17 minutes, totally 20 cycles.

3. 1 μl endonuclease Dpn1 was incorporated to digest parent DNA chain (37° C., 1 h); 1 μl digestion product was placed on ice and incubated with 50 μl XL1-Blue competent cells for 30 minutes, heat shock at 42° C. for 45 seconds, and then taken into ice for 2 minutes;

4. 0.5 ml NZY culture medium was added, the bacteria solution (reactant of step 3, i.e. transformed cells from competent cells) was shaken at 220 rpm and 37° C. for 1 hour; then 50-100 μl reactant was taken out to plank on medium plate (LB culture medium with 1% agar and 50 μg/ml ampicillin, at 37° C. over night);

5. The bacteria was picked out after cultivating 18 hours, the plasmid was abstracted and sequenced to ascertain it had successful mutation;

6. 100 ng mutated plasmid was placed on ice and incubated with 40 μl of BL-21 competent cells for 5.minutes, heat shock at 42° C. for 30 seconds, and then placed on ice for 2 minutes. 160 μl SOC culture medium was added; bacteria was shaken at 220 rpm, 37° C. for 1 hour and taken out to plank on medium plate (LB culture medium with 1% agar, 50 ng/ml ampicillin, at 37° C. cultivating one night); monoclone colonies are picked out for largely reproducing;

7. The bacteria was largely reproduced in 8-10 L FB culture medium, at 250 rpm, 30° C. for 3-4 hours, and warmed to 42° C. at 250 rpm for 0.5 hours and then cooled to 37° C. at 250 rpm for 1.5 hours. The thallus was centrifugated at 4° C., 6000 g for 20 minutes, and then was suspended in 80-100 ml of 50 mM boric acid buffer fluid (pH 9.0, with 2 mM EDTA) at 4° C. After being added in 50 μg PMSF the thallus was ultrasonicated at 4° C., 400 W for 1 minute and repeated 4-5 times with 2-3 minutes interval for maintaining the temperature of the bacteria solution. The cracked thallus was high-speed centrifugated at 4° C., 75,000 g for 90 minutes. The 5,000,000 unit streptomycin sulfate was added into the supernatant to deposit DNA (stiring at 4° C. for 1 hour). After centrifugated at 10000 g, 4° C. for 10 minutes, the supernatant was loaded in bag filter of 15,000 molecular weight and dialysed by 10 L of 50 mM boric acid buffer fluid over night at 4° C.; then centrifuged again at 10000 g, 4° C. for 10 minutes. The supernatant was loaded on CM ion-exchange column. Then the CM ion-exchange column was washed thoroughly and the novel antibiotic was eluted by 0.3 M NaCl+50 mM boric acid buffer fluid. Corresponding to the above two kinds of recombinant plasmid, the novel antibiotics were named PMC-AM1 and PMC-AM2 of which the amino acid sequences were set forth in Seq ID No.6 and Seq ID No.8 respectively.

The AM1 was a peptide chain comprising of the peptides of the first complementarity determining domain in variable region of the heavy chain, the peptide of the second frame region of the heavy chain and the peptide of the third complementarity determining domain in variable region of the light chain. The three domains linked to form a linear molecule as follow N-VHCDR1-VHFR2-VLCDR3-C by the C-terminus connected to the N-terminus of the next domain. Its amino acid sequence was set forth in Seq ID No.2. The AM2 was a peptide chain comprising of the peptide of the first complementarity determining domain in variable region of the heavy chain, the peptide of the second frame region of the heavy chain and the peptide of reversed third complementarity determining domain in variable region of the light chain. The linear molecular as follow: N-VHCDR1-VHFR2-reversed (VLCDR3)-C. Its amino acid sequence was set forth in Seq ID No.4. The PMC-AM2 was constructed as a control of the PMC-AM1 for testing the activity of the novel antibiotics when the domains composing the antibody mimetic were connected in different order.

The artificial oligo nucleotide sequences for preparing above two mutation plasmids respectively are as follow:

```
pBHC-PorA 1
                                                                         (SEQ ID NO. 9)
5'-3' gcg aat aag ttc tgg ggt att TCT TAT TGG CTG CAT TGG ATT AAA CAG taa ata aaa tat aag aca
ggc (SEQ ID NO. 10)
3'-5' gcc tgt ctt ata ttt tat tta CTG TTT AAT CCA ATG CAG CCA ATA AGA aat acc cca gaa ctt att
cgc (SEQ ID NO. 11)
5'-3' tgg ctg cat tgg att aaa cag AGA CCT GGT CAG GGA CTG TGG ATC GGA taa ata aaa tat aag aca
ggc (SEQ ID NO. 12)
3'-5' gcc tgt ctt ata ttt tat tta TCC GAT CCA CAG TCC CTG ACC AGG TCT ctg ttt aat cca atg cag
cca (SEQ ID NO. 13)
5'-3' ggt cag gga ctg tgg atc gga TCT CAG TCC ACG CAT GTG CCG AGA ACC taa ata aaa tat aag aca
ggc (SEQ ID NO. 14)
3'-5' gcc tgt ctt ata ttt tat tta GGT TCT CGG CAC ATG CGT GGA CTG AGA tcc gat cca cag tcc ctg
acc pBHC-PorA 2
                                                                         (SEQ ID NO. 15)
5'-3' gcg aat aag ttc tgg ggt att TCT TAT TGG CTG CAT TGG ATT AAA CAG taa ata aaa tat aag aca
ggc (SEQ ID NO. 16)
3'-5' gcc tgt ctt ata ttt tat tta CTG TTT AAT CCA ATG CAG CCA ATA AGA aat acc cca gaa ctt att
cgc (SEQ ID NO. 17)
5'-3' tgg ctg cat tgg att aaa cag AGA CCT GGT CAG GGA CTG TGG ATC GGA taa ata aaa tat aag aca
ggc (SEQ ID NO. 18)
3'-5' gcc tgt ctt ata ttt tat tta TCC GAT CCA CAG TCC CTG ACC AGG TCT ctg ttt aat cca atg cag
cca
```

-continued

```
                                                                   (SEQ ID NO. 19)
5'-3' ggt cag gga ctg tgg atc gga ACC AGA CCG GTG CAT ACG TCC CAG TCT taa ata aaa tat aag aca ggc (SEQ ID NO. 20)
3'-5' gcc tgt ctt ata ttt tat tta AGA CTG GGA CGT ATG CAC CGG TCT GGT tcc gat cca cag tcc ctg acc.
```

Embodiment 2: Inhibiting Effect of the Novel Antibiotic on *Diplococcus meningitides*.

The bacteria was strain No. 29332 *Nesseria meningitidis* (No. 29332 of bacteria Preservation Center in China, i.e. Center of Medical Devices of National Institute for the Control of Pharmaceutical & biological Products, SDA), two microlitres (μl) of bacteria solution ($10^5$ CFU/ml) was added in 10 ml rabbit blood-chocolate medium containing 50 mg beef extract, 100 mg tryptone, 50 mg NaCl, 30 mg $K_2HPO_4$ and 0.5-0.8 ml off fiber rabbit blood. Five groups were prepared. The first group was added 0.3 M NaCl+50 mM boric acid buffer fluid (i.e. blank preservative fluid for the novel antibiotic, by the same volume with the novel antibiotic solution in the group 4 and 5) as control. Penicillin sodium was added in the second group by 5 μg/ml. The novel antibiotic PMC-AM1 was added in the third group by 5 μg/ml. The novel antibiotic PMC-AM2 was added in the forth group by 5 μg/ml. The novel antibiotic PMC-AM1 was added in the fifth group by 10 μg/ml.

Figure 4:
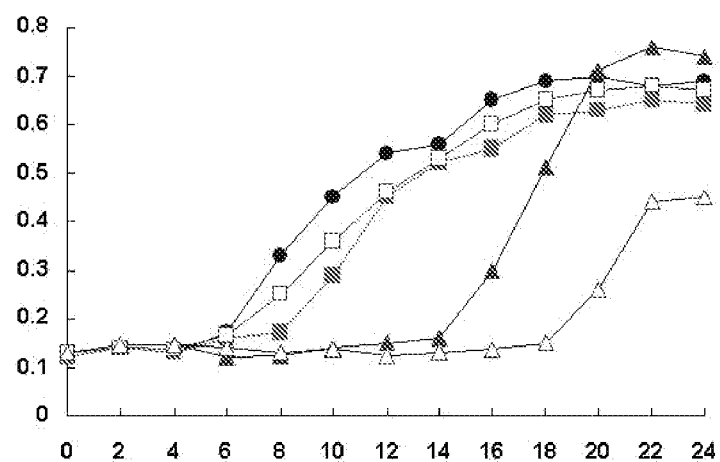
FIG. 4 shows the result of experiment for inhibiting ability of the novel antibiotic PMC-AM1 to *Diplococcus intracellularis*. In the curve, from left to right shows the control, 5 μg/ml Ampicillin, 5 μg/ml PMC-AM2, 5 μg/ml PMC-AM1, 10 μg/ml PMC-AM1. The horizontal ordinate shows the time for bacteria growth by hours; the longitudinal ordinate shows optical density of the bacteria medium at 600 nm, indicating the quantity of bacteria growth.

Reactant liquid of the above five groups were respectively put into 100 ml conical flask, and cultured at 37° C. by 200 rpm 100 μl culture solution was sampled per hour and added onto 96-pore ELISA plate for measuring bacteria grown cloudiness by spectrophotometer (A595 nm) color comparison. The bacteria-growth curve was drawn up to compare the bacteriostasis efficacy of novel antibiosis. The result, as shown in FIG. 4, showed that *Nesseria meningitidis* can only be restrained by PMC-AM1.

Embodiment 3. Contrast Experiment of the Minimum Inhibitory Concentration of the Novel Antibiotic and Normal Antibiotics on Multi-drug Resistant *Pseudomonas aeruginosa*.

Testing the minimum inhibitory concentration (MIC) of the novel antibiotic by the agar dilution method. The bacteria was inoculated on the surface of agar plate containing different concentrations of drugs by multipoint inoculate instrument (Deneley A400). The bacteria concentration on per point was $10^5$ CFU/ml. After incubated at 37° C. for 18-24 hours, the result can be observed. The least concentration of drugs in the plating medium without bacteria growth was Minimum Inhibitory Concentration (MIC) of the drug to the said bacteria.

Experimental strain was multi-drug resistant *Pseudomonas aeruginosa* which was a clinical isolated strain (isolated by West China Hospital, No. 13578) using MH medium (per 100 ml containing 500 mg beef extract, 1.75 g casein acid hydrolyzate, 150 mg soluble starch and 1.7 g gelose).

Figure 5:
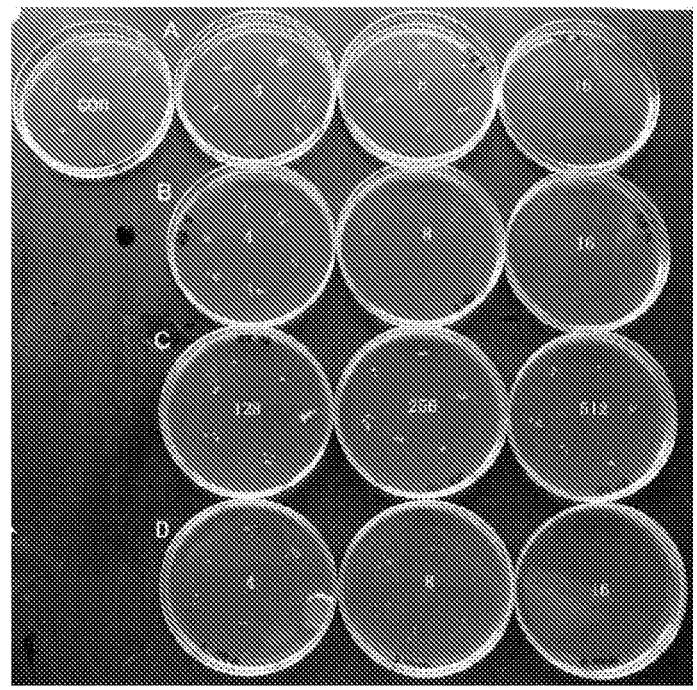
FIG. 5 shows the minimum inhibitory concentration value (MIC) of the novel antibiotic tested by Agar dilution method. The plates shows the MIC of the drugs to multi-drug resistant *Pseudomonas aeruginosa:* Con was blank control, (A) the MIC of ceftazidime was 16 μg/ml, (B) the MIC of levofloxacin was 8 μg/ml, (C) the MIC of gentamicin was greater than 512 μg/ml, (D) the MIC of PMC-AM1 was 8 μg/ml.

As the result showed in FIG. 5, the MIC of the novel antibiotic (D) PMC-AM1 on multi-drug resistant *Pseudomonas aeruginosa* was 8 μg/ml, ceftazidime (A) was 16 μg/ml, levofloxacin(B) was 8 μg/ml, and gentamicin(C) was greater than 512 μg/ml. If in terms of molecular weight standard, the MIC of PMC-AM1 on multi-drug resistant *Pseudomonas aeruginosa* was 0.23 nMol, ceftazidime (A) was 29.3 nMol, levofloxacin was 43.2 nMol, and gentamicin(C) was greater than 890 nMol, i.e. the antibacterial effect of PMC-AM1 on multi-drug resistant *Pseudomonas aeruginosa* was stronger 127-3800 times than ceftazidime, levofloxacia and gentamicin.

Embodiment 4. Contrast Experiment of the Antibacterial Activity in vitro Between the Novel. Antibiotic of this Invention and Normal Antibiotics Testing the minimum inhibitory concentration (MIC) of the novel antibiotic by the agar dilution method. The bacteria was inoculated on the surface of agar plate containing different concentrations of drugs by multipoint inoculate instrument (Deneley A400). The bacteria concentration per point was $10^5$ CFU/ml. After incubated at 37° C. for 18-24 hours, the result can be observed. The least concentration of drugs in the plating medium without bacteria growth was Minimum Inhibitory Concentration (MIC) of the drug to the said bacteria.

Experimental strains were multi-drug resistant *Pseudomonas aeruginosa* which is a clinical isolated strain (isolated by West China Hospital, No. 13578) using MH medium (Per 100 ml containing 500 mg beef extract and 1.75 g_casein acid hydrolyzate, 150 mg soluble starch, 1.7 g_gelose), methicillin-resistant *Staphylococcus aureus* (ATCC BAA-42) using BM medium (Per 100 ml containing 1 g tryptone, 0.5 g yeast powder, 0.1 g glucose, 100 mg $KH_2PO_4$, Ig NaCL and 1 g_gelose), vancomycin-resistant *Enterococcus faecalis* (ATCC 700802) using the MH medium; *Nesseria meningitidis* (No. 29332 of bacteria Preservation Center in China, i.e. Center of Medical Devices of National Institute for the Control of Pharmaceutical & biological Products, SDA) using the same medium used in the embodiment 2 (in addition added Columbia blood agar base 3.9 g).

Figure 6:
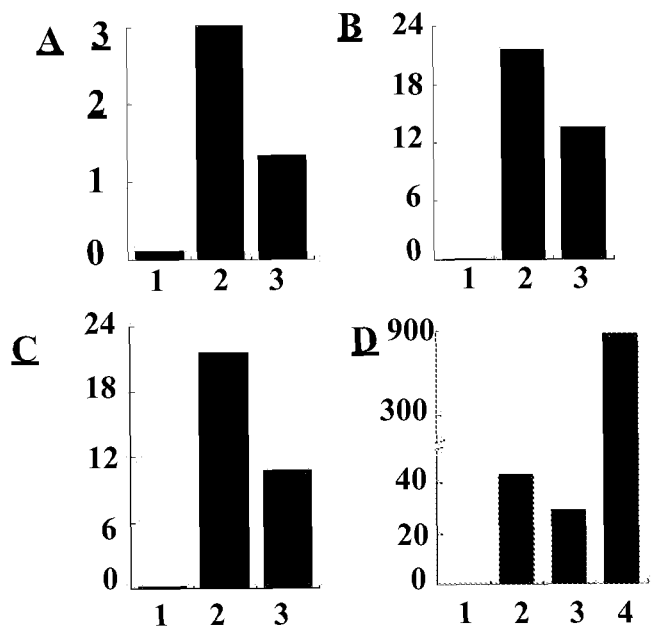
FIG. 6 shows the comparison experiment of minimum inhibitory concentration of the novel antibiotic of this invention and commonly used antibiotics to methicillin-resistant *Staphylococcus aureus* (ATCC BAA-42), vancomycin-resistant *Enterococcus faecalis* (ATCC 700802), multi-drug resistant *Pseudomonas aeruginosa* (isolated by West China Hospital, No. 13578) and *Nesseria meningitidis* (No.29332 of bacteria Preservation Center in China, i.e. Center of Medical Devices of National Institute for the Control of Pharmaceutical & biological Products, SDA).

The result shown in FIG. 6, FIG. A of which showed the result of *Nesseria meningitidis:* (1) PMC-AM1, MIC=0.11 nMol, (2) ceftazidime, MIC=3.02 nMol, (3) ampicillin, MIC=1.35 nMol. FIG. B showed the result of vancomycin-resistant *Enterococcus faecalis:* (1) PMC-AM1, MIC=0.23 nMol, (2) vancomycin, MIC=21.54 nMol, (3) ampicillin, MIC=10.78 nMol. FIG. C showed the result for methicillin-resistant *Staphylococcus aureus:* (1) PMC-AM1, MIC=0.06 nMol, (2) ampicillin MIC=21.55 nMol, (3) oxacillin, MIC=14.1 nMol. FIG. D showed the result for multi-drug resistant *Pseudomonas aeruginosa:* (1) PMC-AM1, MIC=0.91 nMol, (2) levofloxacin, MIC=43.2 nMol, (3) ceftazidime, MIC=29.3 nMol (4) gentamicin, MIC>889.4 nMol.

Embodiment 5. Contrast Experiments of the Antibacterial Activity in vitro Between the Novel Antibiotic of this Invention, the Polypeptide Anti-*Staphylococcal aureus* and Wild-type Colicin Ia.

Testing the minimum inhibitory concentration (MIC) of the novel antibiotic by the agar dilution method. The least concentration of drugs in the plating medium without bacteria growth was Minimum Inhibitory Concentration (MIC) of the drug to the said bacteria.

Experimental strains were multi-drug resistant *Pseudomonas aeruginosa* (isolated by West China Hospital, No.

13578), methicillin-resistant *Staphylococcus aureus* (ATCC BAA-42), vancomycin-resistant *Enterococcus faecalis* (ATCC 700802), using MH medium; *Nesseria meningitidis* (No. 29332 of bacteria Preservation Center in China, i.e. Center of Medical Devices of National Institute for the Control of Pharmaceutical & biological Products, SDA) using the same medium used in the embodiment 4.

The results shown in FIG. 7, FIG. 7A of which showed the result for vancomycin-resistant *Enterococcus faecalis:* (1) the polypeptide anti-*Staphylococcal aureus*, MIC=0.91 nMol, (2) the wildtype Colicin Ia, MIC=0.91 nMol, (3) PMC-AM1,MIC=0.23 nMol. FIG. B showed the result for methicillin-resistant *Staphylococcus aureus:* (1) the polypeptide anti-*Staphylococcal aureus,* MIC=0.06 nMol, (2) the wildtype Colicin Ia, MIC=0.23 nMol, (3) PMC-AM1, MIC=0.06 nMol. FIG. C showed the result for multidrug resistance *Pseudomonas aeruginosa:* (1) the polypeptide anti-*Staphylococcal aureus*, MIC=0.91 nMol, (2) the wildtype Colicin Ia, MIC=0.91 nMol, (3) PMC-AM1, MIC=0.23 nMol Embodiment 6. In vivo Protection Experiments of the Novel Antibiotics for Animals Infected by *Nesseria meningitidis*.
Experimental Materials
Drugs: PMC-AM1, gentamicin, ampicillin.
Experimental Bacteria
*Nesseria meningitidis* (No. 29332 of Bacteria Preservation Center in China, i.e. Center of Medical Devices of National Institute for the Control of Pharmaceutical & biological Products, SDA).
Experimental Methods As shown in FIG. 7, 40 mice were divided into four experimental groups, 10 mice in each group. The mice were given an intraperitoneal injection of glucose solution of ferrous by 20 mg/kg, and 1 hour later an intraperitoneal injection of 0.5 ml of bacteria culture containing 1 share of *Nesseria meningitidis* cultrue solution (its CFU was $2.36 \times 10^9$/ml) and 1.5 share of 5% dry yeast solution. One hour later after being given intraperitoneal injection of fatal dose of the bacteria culture, the mice in experimental group were given an intravenous injection of the drugs and the mice in control group were given an intravenous injection of normal saline, all drugs were injected by 1.5 mg/kg), observation every 2 hours for 8 days, the death of mice as the positive results.

In the FIG. 7, 1.PMC-AM1 means the novel antibiotic obtained in this invention; 2. Gen means gentamicin; 3. PEN mean penicillin; 4. Con.means control.
Results.

As the survive curve shown in FIG. 7, after being given intraperitoneal injection of fatal dose of *Neisseria meningitides* solution, 1). mice in the control group all died in two days, 2). mice in penicillin group all died in two days, 3) mice in gentamicin group had 50% survival rate in 8 days, 4) mice in PMC-AM1 group had 90% survival rate in 8 days.

The result indicates the novel antibiotic PMC-AM1 obtained in the present invention performed superior protection activity in vivo on mice infected by fatal dose of *Nesseria meningitidis* than traditional antibiotics.
Embodiment 7: The Effect of the Novel Antibiotic on *Mycobacterium tuberculosis*'s Growth.

The *Mycobacterium tuberculosis* are the standard strains H37Rv, clinical drug-resistant strain94120, rifampicin-resistant strain94140 and isoniazid-resistant strain 94125, which are preserved in General Hospital of PLA General Staff Department (PLA No. 309 Hospital).

1. The bacteria solution of *Mycobacterium tuberculosis* H37Rv preserved at −70° C. and clinical drug-resistant strains No. 94120 preserved on Roche slant medium at 4° C. were inoculated on a Roche slant medium and incubated at 37° C. for 2 weeks.
2. The bacteria lawn was scraped and grinded in PBS solution to prepare bacteria suspension of $10^{-2}$ mg/ml;
3. 0.1 ml bacteria solution prepared in step 2 was respectively added in tubes with 3 ml 7H9 liquid medium and drugs or control solution, (Inoculum quantity was about $10^{4-5}$ CFU). 0.1 ml bacteria solution prepared in step 2 was added in tubes with 3 ml 7H9 medium, totally 5 groups. The first group as control was added 0.3M NaCl+50 mM boric acid buffer (by the same volume with the PMC-AM1 in group 5), the second group was added wildtype Colicin Ia by 0.5 μg/ml, the third group was added rifampicin by 0.5 μg/ml, the forth group was added isoniazid by 0.5 μg/ml, and the fifth group was added PMC-AM1 by 0.5 μg/ml. Cultured at 37° C. for 4 weeks, judge the effect of the novel antibiotics on the *Mycobacterium tuberculosis*' growth according to the bacteria lawn's outgrowth Result shown in FIG. 9.A, 0.5 μg/ml rifampicin could not inhibit the growth of the strain94120, but the PMC-AM1 of the same concentration could inhibit, i.e. there was no growth of bacteria lawn in the tube added PMC-AM1, but a mass of bacteria lawn could be seen in the tubes of control and added rifampicin.

In order to determine the role of the PMC-AM1 is bacteriostatic or bactericidal. All of bacteria culture solution of strain H37Rv in PMC-AM1 group which had no growth of bacteria lawn was centrifugated and abandoned supernatant and then added in 3 ml of fresh 7H9 medium to observe whether the *Mycobacterium tuberculosis* will grow. If no growth, we may affirm that the PMC-AM1 has a bactericidal effect. The experiment designed as follow: taking four tubes with 3 ml 7H9 medium as four treatments, 0.1 ml bacteria culture solution of strain H37Rv prepared in step 2 was added in the tube1, 2 and 3, and the tube 4 was added the centrifugation of 3 ml bacteria culture solution of strain H37Rv in PMC-AM1 group of step 3 which has no growth of bacteria lawn. The tube 1 was blank control, the tube 2 as control was added 0.3M NaCl+50 mM boric acid buffer fluid by the same volume with the PMC-AM1 solution of the step3, and the third group was added wild-type Colicin Ia by 1 μg/ml. The four tubes were cultured at 37° C. for 120 days, there was a mass of bacteria lawn growing in tube 1~3, but there was always no growth of bacteria lawn in tube 4, (as shown in FIG. 9, B). The result indicates the effect of PMC-AM1 on *Mycobacterium tuberculosis* is bactericidal effect rather than simply antibacterial effect.

Embodiment 8. In vivo Protection Experiments of the Novel Antibiotics to Animals Infected by *Mycobacterium tuberculosis*.
Experimental Materials
Drugs: PMC-AM1, wildtype Colicin Ia, rifampicin, isoniazid.
Experimental bacteria: *Mycobacterium tuberculosis* (the standard strains H37RV).
Experimental Methods 1. The *Mycobacterium tuberculosis* was inoculated in 7H9 mediums to cultrue, and then weighed the wet weight of bacteria lawn and prepared 10 μg/ml bacteria solution. 100 μl the bacteria solution (about $10^{4-5}$ CFU/ml) was added in 3 ml 7H9 medium and incubated at 37° C. for 3 weeks.
2. The *Mycobacterium tuberculosis* bacterium on top of the 7H9 medium was picked out and added into PBS buffer, centrifuged at 2000 g for 5 minutes. The supernatant was removed, and the centrifugation was weighed the wet weight, then added in PBS buffer to dilute to 1 mg/mL (about 10$^{5-6}$ CFU/ml). After grinded, 0.2 ml the bacteria solution was used for injecting each mouse.

3. 60 female BalB/c mice given intravenous injection of *Mycobacterium tuberculosis* solution in step 2, each weighing 17-19 g, were divided into 6 groups of 10 each. The daily injection volume to the mice was as follow: group A were injected the normal saline by the same volume with the drugs, group B were injected the rifampin by 20 μg/g, group C were injected the isoniazid by 25 μg/g, group D were injected the wildtype Colicin Ia by 20 μg/g, group E were injected the PMC-AM1 by 10 μg/g, and group F were injected the PMC-AM1 by 40 μg/g;

Data Acquisition:

1. Giving intraperitoneal injection 6 times per week, and observing mice's coat, appetite, activity and so on.
2. 5 weeks after being given intraperitoneal injection, the mice were artificially killed (wherein 3 mice in control group, 1 mouse in wildtype Colicin Ia group had died gradually from the forth week). Weighed and dissected the dead mice to observe the organs' change and weighed the weight of the organs (Lung, liver and spleen).
3. Analysis of the organs' pathological section.

The Result

FIG. 10 illustrated the observation of the mice's lung: in which, A showed the lungs of three control mice, the arrows indicating TB nodules, we can see a mass of TB nodules. B showed the lungs of mice treated by rifampin, there was no TB nodules as appeared in control mice's lung's on the whole, but there was necrosis (as the arrow indicating) on the lung of one mouse, C showed the lungs of three mice treated by low dose of PMC-AM1, there were no TB nodules and necrosis by a general view.

FIG. 11 showed the foresaid mice's lung by microscope: A showed the lung of one control mouse, and we can see the basic organization of the lung in which the alveolar had all been replaced by exudate cells and tuberculosis nodular; B showed that the pathological process of one mouse lung treated by wildtype Colicin Ia was in accord with t the control mice, but the injury was little slighter than the control mouse's. C showed the lung of one mouse treated by rifampicin, we can see the lung's organization was intact basically, but had a mass of cellular infiltration in parts. D showed the lung of one mouse treated by PMC-AM1, we can see the lung's structure was intact but had a little of cellular infiltration in parts. The magnification was 200, the scale in FIG. A was 100 μm.

During experiment, the weight of mice treated by rifampicin, isoniazid or PMC-AM1 were all rise. The result of experiment in vivo is in accord with embodiment 7, indicating the PMC-AM1 can resist to infection of *Mycobacterium tuberculosis* in vivo.

The invention claimed is:

1. An antibiotic comprising:
   an antibody mimetic covalently bonded to a carboxyl end of a colicin polypeptide or a channel-forming domain polypeptide of a colicin, wherein said colicin is selected from the group consisting of colicin E1, Ia, Ib, A, B, N; wherein an amino acid sequence of said antibody mimetic is SEQ ID NO: 2.

2. The antibiotic of claim 1, wherein said colicin is Ia.

3. A nucleic acid molecule encoding an antibiotic, comprising:
   a nucleotide sequence encoding for:
   an antibody mimetic covalently bonded to a carboxyl end of a colicin polypeptide or a channel-forming domain polypeptide of a colicin, wherein said colicin is selected from the group consisting of colicin E1, Ia, Ib, A, B, N; wherein an amino acid sequence of said antibody mimetic is SEQ ID NO: 2.

4. The nucleic acid molecule of claim 3, its nucleotide sequence is SEQ ID NO.5.

5. The nucleic acid molecule of claim 4, wherein the nucleotide sequence is in a recombinant plasmid.

6. A preparation method of an antibiotic, the method comprising:
   transfecting a recombinant plasmid having a nucleotide sequence of SEQ ID NO.5 into an expression system, and
   separating and purifying a polypeptide expressed from the nucleotide sequence to obtain the antibiotic, the antibiotic comprising:
   an antibody mimetic covalently bonded to a carboxyl end of a colicin polypeptide or a channel-forming domain polypeptide of a colicin, wherein said colicin is selected from the group consisting of colicin E1, Ia, Ib, A, B, N; wherein an amino acid sequence of said antibody mimetic is SEQ ID NO: 2.

7. A medicament comprising:
the antibiotic of claim 1 in an amount sufficient for an antibacterial medicament.

8. The medicament of claim 7, wherein said antibacterial medicament is suitable for killing *Neisseria meningitides*, vancomycin-resistant *Enterococcus faecalis*, methicillin-resistant *Staphylococcus aureus*, multidrug-resistance *Pseudomonas aeruginosa* or *Mycobacterium tuberculosis*.

9. The antibiotic of claim 1, the antibiotic having the amino acid sequence of SEQ ID NO: 6.

10. The nucleic acid molecule of claim 3, the antibiotic having the amino acid sequence of SEQ ID NO: 6.

11. The method of claim 6, the antibiotic having the amino acid sequence of SEQ ID NO: 6.

* * * * *

UNITED STATES PATENT AND TRADEMARK OFFICE
CERTIFICATE OF CORRECTION

PATENT NO. : 9,073,989 B2
APPLICATION NO. : 13/013693
DATED : July 7, 2015
INVENTOR(S) : Qiu It is certified that error appears in the above-identified patent and that said Letters Patent is hereby corrected as shown below:

On the Title Page, in Item (73), under "Assignee", in Column 1, Line 1, delete "LAB, LTD." and insert -- LAB. LTD. --, therefor.

On the Title Page, in Item (56), under "PUBLICATIONS", in Column 1, Line 1, delete "Biophys. Biophys. Chem." and insert -- Biophys. Chem. --, therefor.

On the Title Page, in Item (57), under "ABSTRACT", in Column 2, Line 4, delete "a antibody" and insert -- an antibody --, therefor.

In The Specification

In Column 1, Line 54, delete "porins on outer membran" and insert -- porins in outer membrane --, therefor.

In Column 3, Lines 59-60, delete "multi-drugresistant" and insert -- multi-drug resistant --, therefor.

In Column 3, Line 65, delete "tuberculosisas," and insert -- tuberculosis, --, therefor.

In Column 4, Line 67, delete "meningitidi:" and insert -- meningitidis: --, therefor.

In Column 5, Line 21, delete "concentration(nMol);" and insert -- concentration (nMol); --, therefor.

In Column 5, Line 42, delete "tuberculosisas." and insert -- tuberculosis. --, therefor.

In Column 6, Line 14, delete "Strategene" and insert -- Stratagene --, therefor.

In Column 6, Line 24, delete "Strategene" and insert -- Stratagene --, therefor.

In Column 6, Lines 63-64, delete "monoclone" and insert -- monoclonal --, therefor.

Signed and Sealed this
Eighth Day of March, 2016

Michelle K. Lee
*Director of the United States Patent and Trademark Office*

CERTIFICATE OF CORRECTION (continued)
U.S. Pat. No. 9,073,989 B2

In Column 7, Line 10, delete "(stiring" and insert -- (stirring --, therefor.

In Column 10, Line 13, delete "levofloxacia" and insert -- levofloxacin --, therefor.

In Column 10, Line 16, delete "Novel." and insert -- Novel --, therefor.

In Column 10, Line 17, delete "Antibiotics" and insert -- Antibiotics. --, therefor.

In Column 11, Line 20, delete "nMol" and insert -- nMol. --, therefor.

In Column 11, Lines 36-37, delete "meningitidis cultrue" and insert -- meningitidis culture --, therefor.

In Column 11, Line 48, delete "Results." and insert -- Results --, therefor.

In Column 12, Line 19, delete "outgrowth" and insert -- outgrowth. --, therefor.

In Column 12, Line 59, delete "cultrue," and insert -- culture, --, therefor.

SEQUENCE LISTING

```
<160> NUMBER OF SEQ ID NOS: 20

<210> SEQ ID NO 1
<211> LENGTH: 81
<212> TYPE: DNA
<213> ORGANISM: Artificial Sequence
<220> FEATURE:
<223> OTHER INFORMATION: The nucleotide sequence of antibody mimetic AM1

<400> SEQUENCE: 1
tcttattggc tgcattggat taaacagaga cctggtcagg gactgtggat cggatctcag      60
tccacgcatg tgccgagaac c                                               81

<210> SEQ ID NO 2
<211> LENGTH: 27
<212> TYPE: PRT
<213> ORGANISM: Artificial Sequence
<220> FEATURE:
<223> OTHER INFORMATION: The amino acid sequence of antibody mimetic AM1

<400> SEQUENCE: 2

Ser Tyr Trp Leu His Trp Ile Lys Gln Arg Pro Gly Gln Gly Leu Trp
1               5                   10                  15

Ile Gly Ser Gln Ser Thr His Val Pro Arg Thr
            20                  25

<210> SEQ ID NO 3
<211> LENGTH: 81
<212> TYPE: DNA
<213> ORGANISM: Artificial Sequence
<220> FEATURE:
<223> OTHER INFORMATION: The nucleotide sequence of antibody mimetic AM2

<400> SEQUENCE: 3
tcttattggc tgcattggat taaacagaga cctggtcagg gactgtggat cggaaccaga      60
ccggtgcata cgtcccagtc t                                               81
```

-continued

<210> SEQ ID NO 4
<211> LENGTH: 27
<212> TYPE: PRT
<213> ORGANISM: Artificial Sequence
<220> FEATURE:
<223> OTHER INFORMATION: The amino acid sequence of antibody mimetic AM2

<400> SEQUENCE: 4

Ser Tyr Trp Leu His Trp Ile Lys Gln Arg Pro Gly Gln Gly Leu Trp
1               5                   10                  15

Ile Gly Thr Arg Pro Val His Thr Ser Gln Ser
            20                  25

<210> SEQ ID NO 5
<211> LENGTH: 1959
<212> TYPE: DNA
<213> ORGANISM: Artificial Sequence
<220> FEATURE:
<223> OTHER INFORMATION: The nucleotide sequence of antibiotic PMC-AM1

<400> SEQUENCE: 5

| | | | | | | |
|---|---|---|---|---|---|---|
| atgtctgacc | ctgtacgtat | tacaaatccc | ggtgcagaat | cgctggggta | tgattcagat | 60 |
| ggccatgaaa | ttatggccgt | tgatatttat | gtaaaccctc | cacgtgtcga | tgtctttcat | 120 |
| ggtaccccgc | tgcatggag | ttccttcggg | aacaaaacca | tctgggggcgg | aaacgagtgg | 180 |
| gttgatgatt | cccaacccg | aagtgatatc | gaaaaaggg | acaaggaaat | cacagcgtac | 240 |
| aaaaacacgc | tcagcgcgca | gcagaaagag | aatgagaata | agcgtactga | agccggaaaa | 300 |
| cgcctctctg | cggcgattgc | tgcaaggaa | aaagatgaaa | acacactgaa | acactccgt | 360 |
| gccggaaacg | cagatgccgc | tgatattaca | cgacaggagt | tcagactcct | gcaggcagag | 420 |
| ctgagagaat | acggattccg | tactgaaatc | gccggatatg | acgccctccg | gctgcataca | 480 |
| gagagccgga | tgctgtttgc | tgatgctgat | tctcttcgta | tatctccccg | ggaggccagg | 540 |
| tcgttaatcg | aacaggctga | aaacggcag | aaggatgcgc | agaacgcaga | caagaaggcc | 600 |
| gctgatatgc | ttgctgaata | cgagcgcaga | aaaggtattc | tggacacccg | gttgtcagag | 660 |
| ctggaaaaaa | atggcgggc | agcccttgcc | gttcttgatg | cacaacaggc | ccgtctgctc | 720 |
| gggcagcaga | cacggaatga | cagggccatt | tcagaggccc | ggaataaact | cagttcagtg | 780 |
| acggaatcgc | ttaacacggc | ccgtaatgca | ttaaccagag | ctgaacaaca | gctgacgcaa | 840 |
| cagaaaaaca | cgcctgacgg | caaaacgata | gtttcccctg | aaaaattccc | ggggcgttca | 900 |
| tcaacaaatc | attctattgt | tgtgagcggt | gatccgagat | ttgccggtac | gataaaaatc | 960 |
| acaaccagcg | cagtcatcga | taaccgtgca | aacctgaatt | atcttctgag | ccattccggt | 1020 |
| ctggactata | aacgcaatat | tctgaatgac | cggaatccgg | tggtgacaga | ggatgtggaa | 1080 |
| ggtgacaaga | aaatttataa | tgctgaagtt | gctgaatggg | ataagttacg | gcaaagattg | 1140 |
| cttgatgcca | gaaataaaat | cacctctgct | gaatctgcgg | taaattcggc | gagaaataac | 1200 |
| ctcagtgcca | gaacaaatga | gcaaaagcat | gcaaatgacg | ctcttaatgc | cctgttgaag | 1260 |
| gaaaagaga | atatacgtaa | ccagcttttcc | ggcatcaatc | agaagatagc | ggaagagaaa | 1320 |
| agaaaacagg | atgaactgaa | ggcaacgaaa | gacgcaatta | atttcacaac | agagttcctg | 1380 |
| aaatcagttt | cagaaaaata | tggtgcaaaa | gctgagcagt | tagccagaga | gatggccggg | 1440 |
| caggctaaag | ggaagaaaat | acgtaatgtt | gaagaggcat | taaaaacgta | tgaaaagtac | 1500 |
| cgggctgaca | ttaacaaaaa | aattaatgca | aagatcgtg | cagcgattgc | cgcagccctt | 1560 |
| gagtctgtga | agctgtctga | tatatcgtct | aatctgaaca | gattcagtcg | gggactggga | 1620 |

-continued

```
tatgcaggaa aatttacaag tcttgctgac tggatcactg agtttggtaa ggctgtccgg    1680
acagagaact ggcgtcctct ttttgttaaa acagaaacca tcatagcagg caatgccgca    1740
acggctcttg tggcactggt cttcagtatt cttaccggaa gcgctttagg cattatcggg    1800
tatggtttac tgatggctgt caccggtgcg ctgattgatg aatcgcttgt ggaaaaagcg    1860
aataagttct ggggtatttc ttattggctg cattggatta acagagaccc tggtcaggga    1920
ctgtggatcg gatctcagtc cacgcatgtg ccgagaacc                           1959
```

<210> SEQ ID NO 6
<211> LENGTH: 652
<212> TYPE: PRT
<213> ORGANISM: Artificial Sequence
<220> FEATURE:
<223> OTHER INFORMATION: The amino acid sequence of antibiotic PMC-AM1

<400> SEQUENCE: 6

```
Ser Asp Pro Val Arg Ile Thr Asn Pro Gly Ala Glu Ser Leu Gly Tyr
1               5                   10                  15

Asp Ser Asp Gly His Glu Ile Met Ala Val Asp Ile Tyr Val Asn Pro
            20                  25                  30

Pro Arg Val Asp Val Phe His Gly Thr Pro Ala Trp Ser Ser Phe
        35                  40                  45

Gly Asn Lys Thr Ile Trp Gly Gly Asn Glu Trp Val Asp Asp Ser Pro
 50                  55                  60

Thr Arg Ser Asp Ile Glu Lys Arg Asp Lys Glu Ile Thr Ala Tyr Lys
65                  70                  75                  80

Asn Thr Leu Ser Ala Gln Gln Lys Glu Asn Glu Asn Lys Arg Thr Glu
                85                  90                  95

Ala Gly Lys Arg Leu Ser Ala Ala Ile Ala Ala Arg Glu Lys Asp Glu
            100                 105                 110

Asn Thr Leu Lys Thr Leu Arg Ala Gly Asn Ala Asp Ala Ala Asp Ile
        115                 120                 125

Thr Arg Gln Glu Phe Arg Leu Leu Gln Ala Glu Leu Arg Glu Tyr Gly
130                 135                 140

Phe Arg Thr Glu Ile Ala Gly Tyr Asp Ala Leu Arg Leu His Thr Glu
145                 150                 155                 160

Ser Arg Met Leu Phe Ala Asp Ala Asp Ser Leu Arg Ile Ser Pro Arg
                165                 170                 175

Glu Ala Arg Ser Leu Ile Glu Gln Ala Glu Lys Arg Gln Lys Asp Ala
            180                 185                 190

Gln Asn Ala Asp Lys Lys Ala Ala Asp Met Leu Ala Glu Tyr Glu Arg
        195                 200                 205

Arg Lys Gly Ile Leu Asp Thr Arg Leu Ser Glu Leu Glu Lys Asn Gly
    210                 215                 220

Gly Ala Ala Leu Ala Val Leu Asp Ala Gln Gln Ala Arg Leu Leu Gly
225                 230                 235                 240

Gln Gln Thr Arg Asn Asp Arg Ala Ile Ser Glu Ala Arg Asn Lys Leu
                245                 250                 255

Ser Ser Val Thr Glu Ser Leu Asn Thr Ala Arg Asn Ala Leu Thr Arg
            260                 265                 270

Ala Glu Gln Gln Leu Thr Gln Gln Lys Asn Thr Pro Asp Gly Lys Thr
        275                 280                 285

Ile Val Ser Pro Glu Lys Phe Pro Gly Arg Ser Ser Thr Asn His Ser
    290                 295                 300
```

```
Ile Val Val Ser Gly Asp Pro Arg Phe Ala Gly Thr Ile Lys Ile Thr
305                 310                 315                 320

Thr Ser Ala Val Ile Asp Asn Arg Ala Asn Leu Asn Tyr Leu Leu Ser
            325                 330                 335

His Ser Gly Leu Asp Tyr Lys Arg Asn Ile Leu Asn Asp Arg Asn Pro
        340                 345                 350

Val Val Thr Glu Asp Val Glu Gly Asp Lys Lys Ile Tyr Asn Ala Glu
    355                 360                 365

Val Ala Glu Trp Asp Lys Leu Arg Gln Arg Leu Leu Asp Ala Arg Asn
370                 375                 380

Lys Ile Thr Ser Ala Glu Ser Ala Val Asn Ser Ala Arg Asn Asn Leu
385                 390                 395                 400

Ser Ala Arg Thr Asn Glu Gln Lys His Ala Asn Asp Ala Leu Asn Ala
            405                 410                 415

Leu Leu Lys Glu Lys Glu Asn Ile Arg Asn Gln Leu Ser Gly Ile Asn
        420                 425                 430

Gln Lys Ile Ala Glu Glu Lys Arg Lys Gln Asp Glu Leu Lys Ala Thr
    435                 440                 445

Lys Asp Ala Ile Asn Phe Thr Thr Glu Phe Leu Lys Ser Val Ser Glu
450                 455                 460

Lys Tyr Gly Ala Lys Ala Glu Gln Leu Ala Arg Glu Met Ala Gly Gln
465                 470                 475                 480

Ala Lys Gly Lys Lys Ile Arg Asn Val Glu Glu Ala Leu Lys Thr Tyr
            485                 490                 495

Glu Lys Tyr Arg Ala Asp Ile Asn Lys Lys Ile Asn Ala Lys Asp Arg
        500                 505                 510

Ala Ala Ile Ala Ala Leu Glu Ser Val Lys Leu Ser Asp Ile Ser
    515                 520                 525

Ser Asn Leu Asn Arg Phe Ser Arg Gly Leu Gly Tyr Ala Gly Lys Phe
530                 535                 540

Thr Ser Leu Ala Asp Trp Ile Thr Glu Phe Gly Lys Ala Val Arg Thr
545                 550                 555                 560

Glu Asn Trp Arg Pro Leu Phe Val Lys Thr Glu Thr Ile Ile Ala Gly
            565                 570                 575

Asn Ala Ala Thr Ala Leu Val Ala Leu Val Phe Ser Ile Leu Thr Gly
        580                 585                 590

Ser Ala Leu Gly Ile Ile Gly Tyr Gly Leu Leu Met Ala Val Thr Gly
    595                 600                 605

Ala Leu Ile Asp Glu Ser Leu Val Glu Lys Ala Asn Lys Phe Trp Gly
610                 615                 620

Ile Ser Tyr Trp Leu His Trp Ile Lys Gln Arg Pro Gly Gln Gly Leu
625                 630                 635                 640

Trp Ile Gly Ser Gln Ser Thr His Val Pro Arg Thr
            645                 650

<210> SEQ ID NO 7
<211> LENGTH: 1959
<212> TYPE: DNA
<213> ORGANISM: Artificial Sequence
<220> FEATURE:
<223> OTHER INFORMATION: The nucleotide sequence of antibiotic PMC-SA2

<400> SEQUENCE: 7
atgtctgacc ctgtacgtat tacaaatccc ggtgcagaat cgctggggta tgattcagat    60
```

-continued

```
ggccatgaaa ttatggccgt tgatatttat gtaaaccctc cacgtgtcga tgtctttcat      120
ggtaccccgc ctgcatggag ttccttcggg aacaaaacca tctggggcgg aaacgagtgg      180
gttgatgatt ccccaacccg aagtgatatc gaaaaaaggg acaaggaaat cacagcgtac      240
aaaaacacgc tcagcgcgca gcagaaagag aatgagaata agcgtactga agccggaaaa      300
cgcctctctg cggcgattgc tgcaagggaa aaagatgaaa acacactgaa aacactccgt      360
gccggaaacg cagatgccgc tgatattaca cgacaggagt tcagactcct gcaggcagag      420
ctgagagaat acggattccg tactgaaatc gccggatatg acgccctccg gctgcataca      480
gagagccgga tgctgtttgc tgatgctgat tctcttcgta tatctccccg ggaggccagg      540
tcgttaatcg aacaggctga aaacggcag aaggatgcgc agaacgcaga caagaaggcc      600
gctgatatgc ttgctgaata cgagcgcaga aaaggtattc tggacacccg gttgtcagag      660
ctggaaaaaa atggcggggc agcccttgcc gttcttgatg cacaacaggc ccgtctgctc      720
gggcagcaga cacggaatga cagggccatt tcagaggccc ggaataaact cagttcagtg      780
acggaatcgc ttaacacggc ccgtaatgca ttaaccagag ctgaacaaca gctgacgcaa      840
cagaaaaaca cgcctgacgg caaaacgata gtttcccctg aaaaattccc ggggcgttca      900
tcaacaaatc attctattgt tgtgagcggt gatccgagat ttgccggtac gataaaaatc      960
acaaccagcg cagtcatcga taaccgtgca aacctgaatt atcttctgag ccattccggt     1020
ctggactata aacgcaatat tctgaatgac cggaatccgg tggtgacaga ggatgtggaa     1080
ggtgacaaga aaatttataa tgctgaagtt gctgaatggg ataagttacg caaagattg      1140
cttgatgcca gaaataaaat cacctctgct gaatctgcgg taaattcggc gagaaataac     1200
ctcagtgcca gaacaaatga gcaaaagcat gcaaatgacg ctcttaatgc cctgttgaag     1260
gaaaaagaga atatacgtaa ccagctttcc ggcatcaatc agaagatagc ggaagagaaa     1320
agaaaacagg atgaactgaa ggcaacgaaa gacgcaatta atttcacaac agagttcctg     1380
aaatcagttt cagaaaaata tggtgcaaaa gctgagcagt tagccagaga gatgccggg      1440
caggctaaag ggaagaaaat acgtaatgtt gaagaggcat taaaaacgta tgaaaagtac     1500
cgggctgaca ttaacaaaaa aattaatgca aagatcgtg cagcgattgc cgcagccctt      1560
gagtctgtga agctgtctga tatatcgtct aatctgaaca gattcagtcg gggactggga     1620
tatgcaggaa aatttacaag tcttgctgac tggatcactg agtttggtaa ggctgtccgg     1680
acagagaact ggcgtcctct ttttgttaaa acagaaacca tcatagcagg caatgccgca     1740
acggctcttg tggcactggt cttcagtatt cttaccggaa gcgctttagg cattatcggg     1800
tatggtttac tgatggctgt caccggtgcg ctgattgatg aatcgcttgt ggaaaaagcg     1860
aataagttct ggggtatttc ttattggctg cattggatta aacagagacc tggtcaggga     1920
ctgtggatcg gaaccagacc ggtgcatacg tcccagtct                            1959
```

<210> SEQ ID NO 8  
<211> LENGTH: 652  
<212> TYPE: PRT  
<213> ORGANISM: Artificial Sequence  
<220> FEATURE:  
<223> OTHER INFORMATION: The amino acid sequence of antibiotic PMC-AM2

<400> SEQUENCE: 8

```
Ser Asp Pro Val Arg Ile Thr Asn Pro Gly Ala Glu Ser Leu Gly Tyr
1               5                   10                  15

Asp Ser Asp Gly His Glu Ile Met Ala Val Asp Ile Tyr Val Asn Pro
            20                  25                  30
```

-continued

```
Pro Arg Val Asp Val Phe His Gly Thr Pro Pro Ala Trp Ser Ser Phe
        35                  40                  45
Gly Asn Lys Thr Ile Trp Gly Gly Asn Glu Trp Val Asp Asp Ser Pro
 50                  55                  60
Thr Arg Ser Asp Ile Glu Lys Arg Asp Lys Glu Ile Thr Ala Tyr Lys
 65                  70                  75                  80
Asn Thr Leu Ser Ala Gln Gln Lys Glu Asn Glu Asn Lys Arg Thr Glu
                 85                  90                  95
Ala Gly Lys Arg Leu Ser Ala Ala Ile Ala Ala Arg Glu Lys Asp Glu
                100                 105                 110
Asn Thr Leu Lys Thr Leu Arg Ala Gly Asn Ala Asp Ala Ala Asp Ile
                115                 120                 125
Thr Arg Gln Glu Phe Arg Leu Leu Gln Ala Glu Leu Arg Glu Tyr Gly
            130                 135                 140
Phe Arg Thr Glu Ile Ala Gly Tyr Asp Ala Leu Arg Leu His Thr Glu
145                 150                 155                 160
Ser Arg Met Leu Phe Ala Asp Ala Asp Ser Leu Arg Ile Ser Pro Arg
                165                 170                 175
Glu Ala Arg Ser Leu Ile Glu Gln Ala Glu Lys Arg Gln Lys Asp Ala
            180                 185                 190
Gln Asn Ala Asp Lys Lys Ala Ala Asp Met Leu Ala Glu Tyr Glu Arg
        195                 200                 205
Arg Lys Gly Ile Leu Asp Thr Arg Leu Ser Glu Leu Glu Lys Asn Gly
210                 215                 220
Gly Ala Ala Leu Ala Val Leu Asp Ala Gln Ala Arg Leu Leu Gly
225                 230                 235                 240
Gln Gln Thr Arg Asn Asp Arg Ala Ile Ser Glu Ala Arg Asn Lys Leu
                245                 250                 255
Ser Ser Val Thr Glu Ser Leu Asn Thr Ala Arg Asn Ala Leu Thr Arg
                260                 265                 270
Ala Glu Gln Gln Leu Thr Gln Gln Lys Asn Thr Pro Asp Gly Lys Thr
            275                 280                 285
Ile Val Ser Pro Glu Lys Phe Pro Gly Arg Ser Ser Thr Asn His Ser
290                 295                 300
Ile Val Val Ser Gly Asp Pro Arg Phe Ala Gly Thr Ile Lys Ile Thr
305                 310                 315                 320
Thr Ser Ala Val Ile Asp Asn Arg Ala Asn Leu Asn Tyr Leu Leu Ser
                325                 330                 335
His Ser Gly Leu Asp Tyr Lys Arg Asn Ile Leu Asn Asp Arg Asn Pro
            340                 345                 350
Val Val Thr Glu Asp Val Glu Gly Asp Lys Lys Ile Tyr Asn Ala Glu
        355                 360                 365
Val Ala Glu Trp Asp Lys Leu Arg Gln Arg Leu Leu Asp Ala Arg Asn
    370                 375                 380
Lys Ile Thr Ser Ala Glu Ser Ala Val Asn Ser Ala Arg Asn Asn Leu
385                 390                 395                 400
Ser Ala Arg Thr Asn Glu Gln Lys His Ala Asn Asp Ala Leu Asn Ala
                405                 410                 415
Leu Leu Lys Glu Lys Glu Asn Ile Arg Asn Gln Leu Ser Gly Ile Asn
            420                 425                 430
Gln Lys Ile Ala Glu Glu Lys Arg Lys Gln Asp Glu Leu Lys Ala Thr
        435                 440                 445
```

```
Lys Asp Ala Ile Asn Phe Thr Thr Glu Phe Leu Lys Ser Val Ser Glu
            450                 455                 460
Lys Tyr Gly Ala Lys Ala Glu Gln Leu Ala Arg Glu Met Ala Gly Gln
465                 470                 475                 480
Ala Lys Gly Lys Lys Ile Arg Asn Val Glu Glu Ala Leu Lys Thr Tyr
                485                 490                 495
Glu Lys Tyr Arg Ala Asp Ile Asn Lys Lys Ile Asn Ala Lys Asp Arg
            500                 505                 510
Ala Ala Ile Ala Ala Ala Leu Glu Ser Val Lys Leu Ser Asp Ile Ser
                515                 520                 525
Ser Asn Leu Asn Arg Phe Ser Arg Gly Leu Gly Tyr Ala Gly Lys Phe
530                 535                 540
Thr Ser Leu Ala Asp Trp Ile Thr Glu Phe Gly Lys Ala Val Arg Thr
545                 550                 555                 560
Glu Asn Trp Arg Pro Leu Phe Val Lys Thr Glu Thr Ile Ile Ala Gly
                565                 570                 575
Asn Ala Ala Thr Ala Leu Val Ala Leu Val Phe Ser Ile Leu Thr Gly
                580                 585                 590
Ser Ala Leu Gly Ile Ile Gly Tyr Gly Leu Leu Met Ala Val Thr Gly
            595                 600                 605
Ala Leu Ile Asp Glu Ser Leu Val Glu Lys Ala Asn Lys Phe Trp Gly
610                 615                 620
Ile Ser Tyr Trp Leu His Trp Ile Lys Gln Arg Pro Gly Gln Gly Leu
625                 630                 635                 640
Trp Ile Gly Thr Arg Pro Val His Thr Ser Gln Ser
                645                 650

<210> SEQ ID NO 9
<211> LENGTH: 69
<212> TYPE: DNA
<213> ORGANISM: Artificial Sequece
<220> FEATURE:
<223> OTHER INFORMATION: for constructing mutation plasmid pBHC-PorA1
       5'-3'

<400> SEQUENCE: 9
gcgaataagt tctggggtat ttcttattgg ctgcattgga ttaaacagta aataaaatat    60
aagacaggc                                                           69

<210> SEQ ID NO 10
<211> LENGTH: 69
<212> TYPE: DNA
<213> ORGANISM: Artificial Sequence
<220> FEATURE:
<223> OTHER INFORMATION: for constructing mutation plasmid pBHC-PorA1,
       3'-5'

<400> SEQUENCE: 10
gcctgtctta tattttattt actgtttaat ccaatgcagc caataagaaa taccccagaa    60
cttattcgc                                                           69

<210> SEQ ID NO 11
<211> LENGTH: 69
<212> TYPE: DNA
<213> ORGANISM: Artificial Sequence
<220> FEATURE:
<223> OTHER INFORMATION: for constructing mutation plasmid pBHC-PorA1,
       5'-3'

<400> SEQUENCE: 11
```

```
tggctgcatt ggattaaaca gagacctggt cagggactgt ggatcggata aataaaatat    60
aagacaggc                                                             69
```

<210> SEQ ID NO 12
<211> LENGTH: 69
<212> TYPE: DNA
<213> ORGANISM: Artificial Sequence
<220> FEATURE:
<223> OTHER INFORMATION: for constructing mutation plasmid pBHC-PorA1,
      3'-5'

<400> SEQUENCE: 12

```
gcctgtctta tattttattt atccgatcca cagtccctga ccaggtctct gtttaatcca    60
atgcagcca                                                             69
```

<210> SEQ ID NO 13
<211> LENGTH: 69
<212> TYPE: DNA
<213> ORGANISM: Artificial Sequence
<220> FEATURE:
<223> OTHER INFORMATION: constructing mutation plasmid pBHC-PorA1, 5'-3'

<400> SEQUENCE: 13

```
ggtcagggac tgtggatcgg atctcagtcc acgcatgtgc cgagaaccta aataaaatat    60
aagacaggc                                                             69
```

<210> SEQ ID NO 14
<211> LENGTH: 69
<212> TYPE: DNA
<213> ORGANISM: Artificial Sequence
<220> FEATURE:
<223> OTHER INFORMATION: Forconstructing mutation plasmid pBHC-PorA1,
      3'-5'

<400> SEQUENCE: 14

```
gcctgtctta tattttattt aggttctcgg cacatgcgtg gactgagatc cgatccacag    60
tccctgacc                                                             69
```

<210> SEQ ID NO 15
<211> LENGTH: 69
<212> TYPE: DNA
<213> ORGANISM: Artificial Sequence
<220> FEATURE:
<223> OTHER INFORMATION: constructing mutation plasmid pBHC-PorA2, 5'-3'

<400> SEQUENCE: 15

```
gcgaataagt tctggggtat ttcttattgg ctgcattgga ttaaacagta aataaaatat    60
aagacaggc                                                             69
```

<210> SEQ ID NO 16
<211> LENGTH: 69
<212> TYPE: DNA
<213> ORGANISM: Artificial Sequence
<220> FEATURE:
<223> OTHER INFORMATION: For constructing mutation plasmid pBHC-PorA2,
      3'-5'

<400> SEQUENCE: 16

```
gcctgtctta tattttattt actgtttaat ccaatgcagc caataagaaa taccccagaa    60
cttattcgc                                                             69
```

```
<210> SEQ ID NO 17
<211> LENGTH: 69
<212> TYPE: DNA
<213> ORGANISM: Artificial Sequence
<220> FEATURE:
<223> OTHER INFORMATION: For constructing mutation plasmid pBHC-PorA2,
      5'-3'

<400> SEQUENCE: 17
tggctgcatt ggattaaaca gagacctggt cagggactgt ggatcggata aataaaatat    60
aagacaggc                                                           69

<210> SEQ ID NO 18
<211> LENGTH: 69
<212> TYPE: DNA
<213> ORGANISM: Artificial sequence
<220> FEATURE:
<223> OTHER INFORMATION: constructing mutation plasmid pBHC-PorA2, 3'-5'

<400> SEQUENCE: 18
gcctgtctta tatttattt atccgatcca cagtccctga ccaggtctct gtttaatcca    60
atgcagcca                                                           69

<210> SEQ ID NO 19
<211> LENGTH: 69
<212> TYPE: DNA
<213> ORGANISM: Artificial sequence
<220> FEATURE:
<223> OTHER INFORMATION: For constructing mutation plasmid pBHC-PorA2,
      5'-3'

<400> SEQUENCE: 19
ggtcagggac tgtggatcgg aaccagaccg gtgcatacgt cccagtctta aataaaatat    60
aagacaggc                                                           69

<210> SEQ ID NO 20
<211> LENGTH: 69
<212> TYPE: DNA
<213> ORGANISM: Artificial sequence
<220> FEATURE:
<223> OTHER INFORMATION: constructing mutation plasmid pBHC-PorA2, 3'-5'

<400> SEQUENCE: 20
gcctgtctta tatttattt aagactggga cgtatgcacc ggtctggttc cgatccacag    60
tccctgacc                                                           69
```